US007273588B1

(12) United States Patent
Cowles et al.

(10) Patent No.: US 7,273,588 B1
(45) Date of Patent: Sep. 25, 2007

(54) METHODS OF SAMPLING HALOSILANES FOR METAL ANALYTES

(75) Inventors: Daniel C. Cowles, Plano, TX (US); David S. Bollinger, Grapevine, TX (US)

(73) Assignee: Air Liquide America L.P., Houston, TX (US)

( * ) Notice: Subject to any disclaimer, the term of this patent is extended or adjusted under 35 U.S.C. 154(b) by 662 days.

(21) Appl. No.: 10/622,015

(22) Filed: Jul. 17, 2003

(51) Int. Cl.
*G01N 1/22* (2006.01)
*G01N 33/20* (2006.01)
(52) U.S. Cl. .................... 422/83; 422/88; 436/73; 436/77; 436/83; 436/84; 436/100; 436/101; 436/124; 436/125; 436/173; 436/181
(58) Field of Classification Search .................. 422/83, 422/88; 436/73, 76–77, 79–84, 100–101, 436/119, 124, 125, 173, 181
See application file for complete search history.

(56) References Cited

U.S. PATENT DOCUMENTS 4,481,178 A * 11/1984 Kray ........................... 423/342
4,529,707 A * 7/1985 Cowles et al. ................. 436/72
5,723,644 A * 3/1998 Tzou ........................... 556/466

OTHER PUBLICATIONS

Abstract from article entitled "ICP Emission Spectroscopy Determination of Trace Amounts of Manganese, Iron, Chromium, Vanadium, Titanium, Copper, Nickel and Cobalt", Fenxi Huaxue, vol. 8(1), 1980, pp. 44-48.*

Chen et al., "Spectrophotometric Determination of Trace and Ultratrace Levels of Boron in Silicon and Chlorosilane Samples," *Fresenius J. Anal. Chem.*, 340:357-362, 1991.

Cowles and Bollinger, "Point-of-Use Sampling and Metal Analysis for Trichlorosilane," *SEMI Technical Symposium (STS): Innovations in Semiconductor Manufacturing*, Jul. 2002.

Stolyarova and Orlova, "Trichlorosilane and Silicon Tetrachloride Sample Preparation for Trace Boron, Phosphorus, and Arsenic Determination," *J. Anal. Chem.*, 50(2):130-134. 1995.

Wei and Yang, "Determination of Phosphorus and Arsenic in Trichlorosilane by Electrothermal Vaporization-Inductively Coupled Plasma Mass Spectrometry with Prior Concentration by Cuprous Chloride," *Fresenius J. Anal. Chem.*, 353:167-170, 1995.

Presentation of POU Sampling and Metal Analysis of Trichlorosilane at SEMI Semiconductor Equipment and Materials International, Jul. 2002.

* cited by examiner

*Primary Examiner*—Maureen M. Wallenhorst
(74) *Attorney, Agent, or Firm*—Brandon Clark; Elwood Haynes

(57) ABSTRACT

Methods for determining the amount of at least one metal analyte present in a liquid or gas sample of a halosilane supply (e.g., a chlorosilane supply) are disclosed herein. A sample of a halosilane supply is contacted and reacted with an aqueous hydrofluoric acid solution to produce a liquid reaction mixture. Liquid from the liquid reaction mixture is evaporated under controlled temperature and pressure conditions to near dryness. The nearly-dry residue is prepared for spectral analysis. The presence of a detectable amount of at least one metal analyte is determined for the sample.

18 Claims, 5 Drawing Sheets

METHODS OF SAMPLING HALOSILANES FOR METAL ANALYTES

BACKGROUND OF THE INVENTION

The present invention relates generally to methods for sampling a halosilane source, and determining the amount of certain metal analytes present in the source. More particularly, it concerns methods for sampling a trichlorosilane supply used for manufacturing polysilicon, and determining the amount of certain metal dopants present in the sample.

Certain highly reactive compounds, such as boron trifluoride, hydrogen chloride, and trichlorosilane, among others, are reagents that can be used in semiconductor fabrication processes. In the presence of oxygen and/or water, certain such highly reactive compounds can cause the metal of storage canisters (e.g., cylinders) and/or supply lines in the fabrication system to corrode. The introduction of air and/or water into the fabrication system can be due to leaks, cylinder change-outs, exhaustion of a purifier's capacity, and/or human error. Thus, the corrosivity of such compounds dictates careful materials selection and handling methods for the delivery lines between the gas supply and the point of use.

Certain chlorosilane and fluorosilane gases can be used in the processing of certain workpieces, such as semiconductor wafers. One such chlorosilane, trichlorosilane, is a corrosive, liquefied gas that is used in large volumes in the manufacture of semiconductor-grade silicon, and in the chemical vapor deposition (CVD) of epitaxial silicon. In a fab, trichlorosilane is delivered to the tool either as a pressurized liquid, or diluted in a carrier gas, such as hydrogen. Since trichlorosilane can be the starting ingredient for wafers, metal impurities present in a trichlorosilane supply may be incorporated into the finished wafer, significantly altering the electrical characteristics of the wafer.

When metal contamination is detected in a product silicon wafer, it can be difficult to determine its origin (e.g., in reactive gas lines or a source cylinder) in the silicon wafer production system. Without being able to efficiently pinpoint the origin of a metal contamination in a polysilicon production system, it may become necessary to replace a gas cylinder, or change out components or whole sections of gas delivery hardware in order to eliminate the contamination. Furthermore, in order to determine that the contamination has been eliminated, time-consuming and costly test wafer production and analysis may be required. A relatively safe, flexible, and more accurate method for collecting a chlorosilane or fluorosilane sample at various points within a silicon wafer production system in order to isolate a contamination source is desirable.

SUMMARY OF THE INVENTION

Certain embodiments of the present invention are directed to methods for measuring at least one metal analyte in a halosilane source. The halosilane source can be, in certain embodiments (e.g., depending on the halosilane), a halosilane canister, a halosilane bulk storage tank, a halosilane supply line, or a deposition chamber. A first sample can be collected from a halosilane source, and the first sample can comprise at least one halosilane having a formula $Si_uCl_vF_wBr_xI_yN_z$, wherein u is 1 or 2; (v+w+x+y) is an integer between 1 and 4+2(u−1), inclusive; each of v, w, x, and y is an integer between 0 and 4+2(u−1), inclusive; z is an integer between 0 and 2u+1, inclusive; (v+w+x+y+z) is equal to 4+2(u−1); and each N can be any organic or inorganic ligand that does not interfere with the reaction of the halosilane with aqueous hydrofluoric acid. Preferably each N is independently selected from the group consisting of hydrogen, methyl, methoxy, ethyl, ethoxy, propyl, propoxy, isopropyl, isopropoxy, n-butyl, butoxy, vinyl, and phenyl. In certain embodiments, each of w, x, and y is 0. In some embodiments, the first sample can also comprise metals that were present in the halosilane source.

The halosilane can be selected from the group consisting of monochlorosilane, dichlorosilane, trichlorosilane, tetrachlorosilane, methyltrichlorosilane, methyldichlorosilane, methylmonochlorosilane, dimethyldichlorosilane, dimethylchlorosilane, trimethylchlorosilane, hexachlorodisilane, triethoxyfluorosilane, phenyldiethoxychlorosilane, tetraethoxysilane, tetrafluorosilane, tetrabromosilane, and tetraiodosilane. In certain embodiments the halosilane can be a chlorosilane. Preferably the halosilane is selected from the group consisting of trichlorosilane, dichlorosilane, tetrachlorosilane, and tetrafluorosilane, and more preferably the halosilane is trichlorosilane.

The first sample can comprise a liquid, gas, or a mixture of liquid and gas. In certain embodiments, the first sample comprises nitrogen gas or hydrogen gas. In certain embodiments, the first sample comprises trichlorosilane and hydrogen, and in other embodiments the first sample comprises trichlorosilane and nitrogen. The first sample can also comprise detectable amounts of certain metal analytes.

The first sample is contacted with an aqueous hydrofluoric acid solution to produce a liquid reaction mixture. The aqueous hydrofluoric acid solution can comprise between about 49 wt % and 5 wt % hydrofluoric acid, preferably between about 35 wt % hydrofluoric acid and 15 wt % hydrofluoric acid, and more preferably the aqueous hydrofluoric acid solution comprises about 25 wt % hydrofluoric acid. In some embodiments, when the volume of the hydrofluoric acid solution is between about 400 and 500 ml, the first sample can be contacted with the aqueous hydrofluoric solution at a flow rate of between about 0.5 g/min and 1 g/min. The solution volume and flow rate can be scaled up, such that in some embodiments, the solution can have a volume as great as 5 liters with a flow rate of between about 5 g/minute and 10 g/minute. When the first sample and the aqueous hydrofluoric acid solution are contacted, a chemical reaction that comprises reacting the halosilane with the aqueous hydrofluoric acid solution can occur, and in certain embodiments, additional chemical reactions can also occur. In certain embodiments, the first sample is contacted with the aqueous hydrofluoric acid solution in the presence of a shield gas. The shield gas can comprise at least one of nitrogen, argon, and helium, and preferably the shield gas consists essentially of nitrogen.

Liquid can be evaporated from the liquid reaction mixture to produce a near-dry residue. Liquid that is evaporated can, in certain embodiments, comprise reaction products from reactions that occurred when the halosilane was contacted with the aqueous hydrofluoric acid solution. In certain embodiments, the near-dry residue comprises at least one metal analyte that was present in the first sample. The near-dry residue can be mixed with a take-up liquid to produce a second sample, at least a portion of which can be analyzed for the presence of a detectable amount of at least one metal analyte. The take-up liquid can, in certain embodiments, comprise nitric acid and hydrogen peroxide. The metal analyte that the second sample is analyzed for can be selected from the group consisting of iron, molybdenum, chromium, zinc, magnesium, tin, titanium, nickel, copper, aluminum, boron, phosphorous, calcium, sodium, manganese, vanadium, potassium, lithium, beryllium, gallium, germanium, arsenic, strontium, zirconium, niobium, cobalt, silver, cadmium, indium, antimony, barium, tantalum, thallium, lead, and bismuth. Preferably the metal analyte is selected from the group consisting of boron, phosphorous, arsenic, antimony, germanium, iron, chromium, nickel, manganese, and molybdenum, and more preferably the metal analyte is selected from the group consisting of boron, phosphorus, and arsenic. Analysis of the second sample can be performed using graphite furnace atomic absorption (GFAA) or inductively coupled plasma-mass spectrometry (ICP-MS). In certain embodiments the analyzing step may be performed using dynamic reaction cell inductively coupled plasma-mass spectrometry (DRC ICP-MS). The analyzing step can be performed using high resolution inductively coupled plasma-mass spectrometry, in some embodiments. Certain embodiments of the present invention are directed to systems for measuring at least one metal analyte in a halosilane source. The system comprises a means for collecting a first sample from a halosilane source. The halosilane source can comprise at least one halosilane having a formula $Si_uCl_vF_wBr_xI_yN_z$, as described above. The system further comprises a means for contacting the first sample with an aqueous hydrofluoric acid solution, thereby producing a liquid reaction mixture; a means for evaporating liquid from the liquid reaction mixture, thereby producing a near-dry residue; a means for mixing the near-dry residue with a take-up liquid, thereby producing a second sample; and a means for analyzing the second sample for the presence of a detectable amount of at least one metal analyte.

Certain embodiments of the present invention are directed to methods for measuring at least one metal analyte in a chlorosilane source. The method can involve collecting a first sample from a chlorosilane source, wherein the first sample comprises at least one chlorosilane (e.g., a silane having a chloro-group). In certain embodiments the chlorosilane can have a formula $Si_uCl_vN_z$, wherein u is 1 or 2; v is an integer between 1 and 4+2(u−1), inclusive; z is an integer between 0 and 2u+1, inclusive; (v+z) is equal to 4+2(u−1); and each N is independently selected from the group consisting of hydrogen, iodo, bromo, fluoro, methyl, methoxy, ethyl, ethoxy, propyl, propoxy, isopropyl, isopropoxy, n-butyl, butoxy, vinyl, and phenyl. Preferably each N is independently selected from the group consisting of hydrogen, methyl, methoxy, ethyl, ethoxy, propyl, propoxy, isopropyl, isopropoxy, n-butyl, butoxy, vinyl, and phenyl. In certain embodiments, the chlorosilane is selected from the group consisting of trichlorosilane, dichlorosilane, and tetrachlorosilane. The first sample may, in certain embodiments, further comprise metal analytes that were present in the chlorosilane source.

The first sample can be contacted with an aqueous hydrofluoric acid solution, thereby producing a liquid reaction mixture. In some embodiments, the aqueous hydrofluoric acid solution comprises about 25 wt % hydrofluoric acid.

At least one chemical reaction can occur as a result of the contacting step, wherein the chemical reaction comprises the chlorosilane reacting with the aqueous hydrofluoric acid solution. In some embodiments, the first sample can be contacted with the aqueous hydrofluoric acid solution in the presence of a shield gas. Liquid (e.g., comprising reaction products) from the liquid reaction mixture can be evaporated to produce a near-dry residue. In some embodiments, the near-dry residue comprises at least one metal analyte. The near-dry residue can be mixed with a take-up liquid, to produce a second sample; and the second sample can be analyzed for the presence of a detectable amount of at least one metal analyte. In certain embodiments, the take-up liquid comprises nitric acid and hydrogen peroxide. In some embodiments, the metal analyte can be selected from the group consisting of boron, phosphorous, arsenic, antimony, germanium, iron, chromium, nickel, manganese, and molybdenum. The analyzing step can be performed using graphite furnace atomic absorption (GFAA) or inductively coupled plasma-mass spectrometry (ICP-MS), in certain embodiments.

Certain embodiments of the present invention are directed to systems for measuring at least one metal analyte in a chlorosilane source. The system comprises a means for collecting a first sample from a chlorosilane source; a means for contacting the first sample with an aqueous hydrofluoric acid solution, thereby producing a liquid reaction mixture; a means for evaporating liquid from the liquid reaction mixture, thereby producing a near-dry residue; a means for mixing the near-dry residue with a take-up liquid, thereby producing a second sample; and a means for analyzing the second sample for the presence of a detectable amount of at least one metal analyte.

Some embodiments are directed to a system for measuring at least one metal analyte from a halosilane source. The system comprises a halosilane source, at least one reaction system, an evaporator and a metal analyte detector. The halosilane source comprises at least one halosilane having a formula $Si_uCl_vF_wBr_xI_yN_z$, as described above. In some embodiments, each of w, x, and y is 0. The halosilane source may also comprise metals and/or other compounds. The halosilane source can, in certain embodiments, be a halosilane canister, a halosilane bulk storage tank (e.g., stand-alone, truck-mounted or railcar-mounted), a halosilane supply line, or a deposition chamber. In certain embodiments, the halosilane source can be a chlorosilane source comprising at least one chlorosilane. A first sample is collected from the halosilane source, and it is contacted with an aqueous hydrofluoric acid solution in the reaction system to produce a liquid reaction mixture. Liquid is evaporated from the liquid reaction mixture to near dryness, and the residue is taken up in a liquid to produce a second sample. At least a portion of the second sample can be analyzed for the presence of at least one metal analyte. The metal analyte detector can, in certain embodiments, analyze the second sample using graphite furnace atomic absorption (GFAA) or inductively coupled plasma-mass spectrometry (ICP-MS). The metal analyte that is detected by the metal analyte detector can be as described above. In some embodiments, the metal analyte detector can detect amounts of metal analytes in the second sample that are less than 1 ppbw.

Certain embodiments comprise a reaction system that comprises a sample introduction line, a shield gas supply line, a shield gas functional line, a connector, and an impinger. At least one of the sample introduction line, the shield gas supply line, the shield gas functional line, the connector, and the impinger can comprise polytetrafluoroethylene (PTFE) or perfluoroalkoxy (PFA), in certain embodiments. The sample introduction line carries the first sample. The shield gas supply line and the shield gas functional line are coupled to each other and carry a shield gas. The shield gas functional line has a longitudinal axis that is parallel to the longitudinal axis of the sample introduction line, and the sample shield gas functional line jackets at least a portion of the sample introduction line. The jacketed portion of the sample introduction line comprises an open end and a continuing end, and the shield gas functional line comprises a first end that is sealed to the continuing end of the portion of the sample introduction line and an open end. The connector connects the shield gas supply line and the shield gas functional line. The connector can be a tee connector, in certain embodiments. The open end of the jacketed portion of the sample introduction line and the open end of the shield gas functional line can be on the same side relative to the connector. The impinger comprises a reaction vessel containing aqueous hydrofluoric acid solution. The aqueous hydrofluoric acid solution can be as described above. The open end of the shield gas functional line and the open end of the jacketed portion of the sample introduction line can be positioned below the surface of the aqueous hydrofluoric acid solution. The open end of the shield gas functional line and the open end of the sample introduction line can be positioned relative to one another such that when the shield gas and the first sample are carried through the reaction system, the shield gas is capable of shielding the first sample when the first sample is contacted with the aqueous hydrofluoric acid solution.

In certain embodiments, a reaction system can further comprise an abatement line and an abatement unit. The abatement unit comprises an abatement vessel and an aqueous caustic solution (e.g., a sodium hydroxide solution). In some embodiments, when the first sample and the aqueous hydrofluoric acid solution are contacted in the impinger an exhaust gas can be produced. The abatement line can carry an exhaust gas from the impinger to the abatement unit, and certain components of the exhaust gas can react with the aqueous caustic solution (e.g., sodium hydroxide solution).

Some embodiments are directed to a system for measuring at least one metal analyte from a chlorosilane source. The system comprises a chlorosilane source, at least one reaction system, an evaporator and a metal analyte detector. The chlorosilane source comprises at least a chlorosilane; it may also comprise metals and/or other compounds. In certain embodiments, the chlorosilane can have a formula $Si_uCl_vN_z$, as described above. A first sample is collected from the chlorosilane source, and it is contacted with an aqueous hydrofluoric acid solution in the reaction system to produce a liquid reaction mixture. In some embodiments, the first sample may also comprise at least one metal analyte. Liquid is evaporated from the liquid reaction mixture to near dryness, and the residue is taken up in a liquid to produce a second sample. At least a portion of the second sample can be analyzed for the presence of at least one metal analyte. The metal analyte detector can, in certain embodiments analyze the second sample using graphite furnace atomic absorption (GFAA) or inductively coupled plasma-mass spectrometry (ICP-MS). The metal analyte that is detected by the metal analyte detector can be as described above. In some embodiments, the metal analyte detector can detect amounts of metal analytes in the second sample that are less than 1 ppbw.

Certain embodiments of the present invention are directed to systems for sampling for at least one metal analyte in a halosilane supply. Such systems can comprise a halosilane supply line to transport at least a halosilane, and a sampling unit coupled with said halosilane supply line. The sampling unit can be capable of collecting a first sample from the halosilane supply line, and the first sample comprises the halosilane, as described above. The first sample may also comprise at least one metal analyte, in certain embodiments. The first sample and an aqueous hydrofluoric acid solution can be contacted in the sampling unit, thereby producing a liquid reaction mixture. At least one chemical reaction that occurs as a result of the contacting step is that halosilane reacts with the aqueous hydrofluoric acid. The sampling unit can comprise a sample introduction line, a shield gas supply line, a shield gas functional line, a connector, and an impinger as described above. In certain embodiments, the sampling unit can also comprise an abatement unit.

Certain embodiments of the present invention can be directed to a system comprising a processing tool to process workpieces, such as semiconductor wafers, a halosilane supply line, and at least one sampling unit. The halosilane supply line supplies at least one of trichlorosilane, dichlorosilane, tetrachlorosilane, and tetrafluorosilane, and preferably it supplies trichlorosilane. The halosilane supply line and the sampling unit can be as described above. In certain embodiments the system further comprises a process controller that is coupled to the processing tool, the halosilane supply line, and the sampling unit. The process controller unit can control an operation of at least one of the processing tool, the halosilane supply line, and the sampling unit.

Certain embodiments of the present invention can provide a safe, flexible method for collecting a halosilane (e.g., chlorosilane) sample at various points within a silicon wafer production system in order to isolate a contamination source.

BRIEF DESCRIPTION OF THE DRAWINGS

The following drawings form part of the present specification and are included to further demonstrate certain aspects of the present invention. The invention can be better understood by reference to these drawings in combination with the detailed description of specific embodiments presented herein.

DESCRIPTION OF ILLUSTRATIVE EMBODIMENTS

Certain embodiments of the present invention are directed to methods for determining the amount of at least one metal analyte present in a liquid, gas, or liquid and gas sample of a halosilane supply (e.g., chlorosilane supply). A sample of a halosilane supply may be contacted and reacted with an aqueous hydrofluoric acid solution to produce a liquid reaction mixture. Liquid from the liquid reaction mixture may be evaporated under controlled temperature and pressure conditions to near dryness. The nearly-dry residue may be prepared for spectral analysis. The presence of a detectable amount of at least one metal analyte may be determined for the sample.

Figure 1:
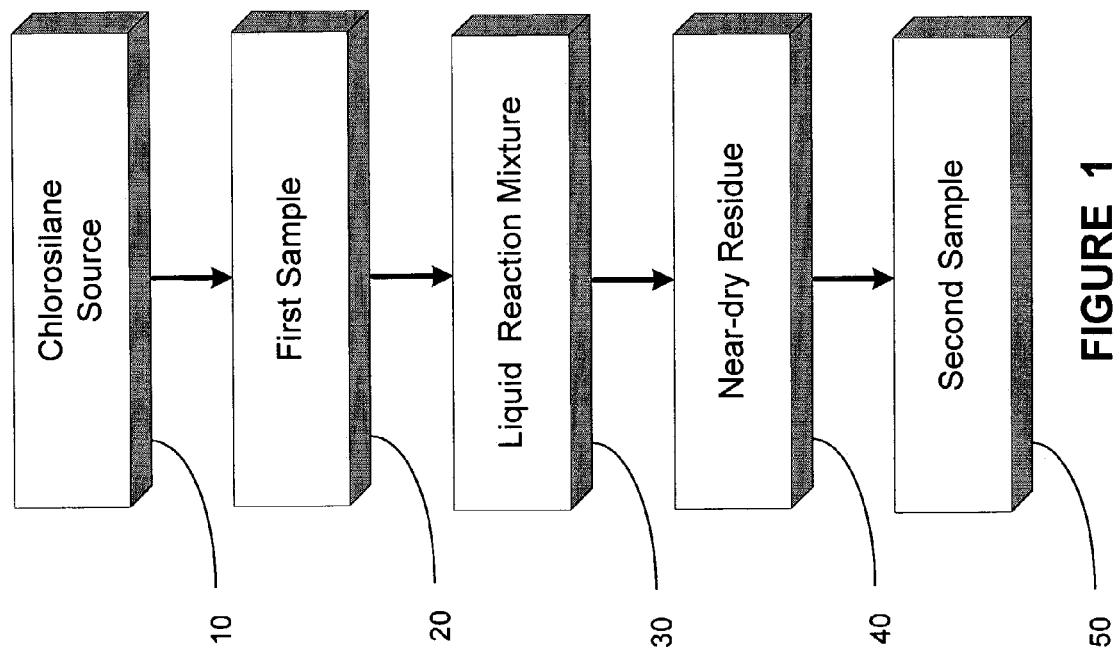
FIG. 1 depicts a scheme for sampling and analyzing metal analytes in accordance with one embodiment of the present invention.

Certain embodiments of the present invention can be better understood with reference to FIG. 1.

A halosilane source 10, such as a chlorosilane source, is provided. The halosilane source 10 can be any known in the art. In one embodiment, the halosilane source 10 is part of a silicon wafer fabrication system. The halosilane source 10 may, for example, be a canister of halosilane, a halosilane bulk storage tank (e.g., stand-alone, truck-mounted, or rail-car-mounted), a supply line carrying a halosilane, or a deposition chamber in which a halosilane is present. In some embodiments, the halosilane source 10 may be a chlorosilane source.

Thus, the halosilane source 10 comprises at least one halosilane. The halosilane can have a formula $Si_uCl_vF_wBr_xI_yN_z$, wherein u is 1 or 2; (v+w+x+y) is an integer between 1 and 4+2(u−1), inclusive; each of v, w, x, and y is an integer between 0 and 4+2(u−1), inclusive; z is an integer between 0 and 2u+1, inclusive; (v+w+x+y+z) is equal to 4+2(u−1); and each N is independently selected from the group consisting of hydrogen, methyl, methoxy, ethyl, ethoxy, propyl, propoxy, isopropyl, isopropoxy, n-butyl, butoxy, vinyl, and phenyl. In certain embodiments, each of w, x, and y in the formula is 0. The halosilane is preferably selected from the group consisting of monochlorosilane, dichlorosilane, trichlorosilane, tetrachlorosilane, methyltrichlorosilane, methyldichlorosilane, methylmonochlorosilane, dimethyldichlorosilane, dimethylchlorosilane, trimethylchlorosilane, hexachlorodisilane, triethoxyfluorosilane, phenyldiethoxychlorosilane, tetraethoxysilane, tetrafluorosilane, tetrabromosilane, and tetraiodosilane. In certain embodiments, the halosilane can be a chlorosilane. In one embodiment, the halosilane is selected from the group consisting of trichlorosilane, dichlorosilane, tetrachlorosilane, and tetrafluorosilane. In one illustrative embodiment of the present invention the halosilane is trichlorosilane. When the halosilane source 10 comprises a single halosilane, especially as part of a fab, it is preferred that the halosilane, such as a chlorosilane, be electronics grade, that is, greater than about 99.9% pure, and more preferably greater than about 99.99% pure. The halosilane source 10 can comprise impurities, such as metals or metal compounds, water, air, carbon, inert gases (e.g., argon or nitrogen), or undesired halosilanes, among others. In certain embodiments, the halosilane source 10 can comprise certain gases, such as hydrogen, helium, argon, or nitrogen. For example, in certain fabs, electronics grade hydrogen saturated (e.g., 20%) with ultra high purity trichlorosilane can be carried through a supply line (e.g., halosilane source 10).

In certain embodiments, undesired halosilane can be produced in small amounts by reaction of a halosilane with itself. For example, an electronics grade trichlorosilane can react with itself to produce small amounts of dichlorosilane and tetrachlorosilane impurities (ref. 1).

$$2SiHCl_3 \rightarrow SiCl_4 + SiH_2Cl_2$$

A first sample 20 may be collected from a halosilane source 10. The first sample 20 collected from the halosilane source 10 comprises at least one halosilane, and can comprise at least one of a gas or a liquid. A first sample 20 can be a gaseous halosilane. In some embodiments, the first sample 20 can comprise at least one halosilane gas and a gas selected from the group consisting of hydrogen, helium, argon, and nitrogen. In one embodiment, the halosilane gas is greater than about 99.9% pure, more preferably greater than about 99.99% pure. Preferably any hydrogen, helium, argon, or nitrogen present in the first sample 20 is electronics grade (e.g., at least about 99.9% pure). In some embodiments, the first sample 20 can be nitrogen saturated with trichlorosilane. For example, a gaseous trichlorosilane can be removed from a canister of trichlorosilane by pressurizing a liquid port on the canister with nitrogen (e.g., 15 psig), and then withdrawing TCS-saturated nitrogen (e.g., 30% TCS by volume) from a gas port. Preferably the trichlorosilane and the nitrogen are electronics grade gases. In certain embodiments, the first sample 20 can comprise hydrogen and a chlorosilane that were collected from a pipeline leading to a process tool. When the first sample 20 comprises hydrogen and trichlorosilane, the sample can comprise 20% (by volume) trichlorosilane saturated hydrogen. Preferably the trichlorosilane and the hydrogen are both electronics grade (e.g., at least about 99.9% pure).

In certain embodiments, the first sample 20 comprises a liquid. For liquid sampling of a canister of a halosilane, the inert gas charge in the as-received canister (typically 20 psig) can provide sufficient driving force to remove a liquid sample. If the inert gas charge is too low to provide a sufficient driving force, the canister can be pressurized with an inert gas at the gas sample port. In one embodiment, when the first sample 20 is a liquid, the liquid comprises greater than about 99.9% liquefied halosilane (e.g., trichlorosilane) or halosilanes, and more preferably greater than about 99.99%. In some cases, a liquid halosilane can be combined with nitrogen gas in a sampling line, and the mixture may comprise, for example, 50% halosilane (e.g., trichlorosilane) by volume, in certain embodiments.

The first sample 20 can comprise impurities that were present in the halosilane source 10. Thus, impurities, such as metals or metal compounds, water, air, carbon, inert gases (e.g., argon or nitrogen), or undesired halosilanes, among others that were present in the halosilane source 10 can be components of the first sample 20.

The first sample 20 is brought into contact with an aqueous solution of hydrofluoric acid to produce a liquid reaction mixture 30. When the first sample 20 and the aqueous hydrofluoric acid are brought into contact with each other, at least one chemical reaction can take place. That is, the halosilane of the first sample 20 reacts with the aqueous hydrofluoric acid.

While not to be bound by theory, trichlorosilane (TCS), a halosilane, can react with water to yield a hydrated silanol and HCl:

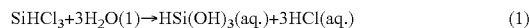

$$SiHCl_3 + 3H_2O(l) \rightarrow HSi(OH)_3(aq.) + 3HCl(aq.) \qquad (1)$$

The hydrolysis of certain other halosilanes can produce similar silanols. Condensation of the silanols can result in the production of polysiloxanes and/or silica solids, which can appear as white flakes (e.g., solids) in the reaction mixture. It is also known that aqueous hydrofluoric acid (HF) can be added to the condensate to dissolve the solids. A reaction that can occur between the condensate and hydrofluoric acid can be represented in part by equation 2.

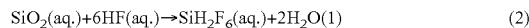

$$SiO_2(aq.) + 6HF(aq.) \rightarrow SiH_2F_6(aq.) + 2H_2O(l) \qquad (2)$$

Reactions 1 and 2 can contribute to overall reaction 3 with an associated reaction exothermicity of 381 kJ/mole.

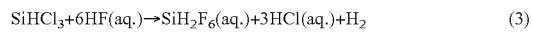

$$SiHCl_3 + 6HF(aq.) \rightarrow SiH_2F_6(aq.) + 3HCl(aq.) + H_2 \qquad (3)$$

Similar chemistry applies to certain other halosilanes. Based on equation 3, there is an upper limit on the quantity of trichlorosilane (e.g., a silane having a chloro-group) that can be consumed by a given volume and concentration of aqueous hydrofluoric acid. Addition of trichlorosilane beyond the stoichiometric limit (i.e., after substantially all hydrofluoric acid has been consumed) results in the appearance of translucent solids. Although these solids can be dissolved by adding more hydrofluoric acid, in practice it is preferable that the amount of trichlorosilane, or other halosilane, reacted with the aqueous hydrofluoric acid remain below the stoichiometric limit to minimize sample-handling steps. The chemistry for the reaction of other halosilanes with aqueous hydrofluoric acid can be similar to that of trichlorosilane, in that fluorosilicic acid can be produced.

That is, in certain reactions a halosilane undergoes hydrolysis to form at least one silanol, which can be condensed to produce fluorosilicic acid in the presence of hydrofluoric acid.

The difference in the weight between the liquid reaction mixture 30 and the aqueous solution of hydrofluoric acid before contact with the first sample 20 can be measured and used to calculate the amount of first sample 20 that was contacted with the acid solution using methods known in the art. Alternatively, if the first sample 20 is being removed from a canister, the amount of the first sample 20 can be determined by analyzing the weight of the canister before and after the first sample 20 is removed.

As discussed above, the first sample 20 is brought into contact with an aqueous solution of hydrofluoric acid to produce a liquid reaction mixture 30 that comprises fluorosilicic acid. The aqueous solution of the hydrofluoric acid can comprise between about 49 wt % and 5 wt % hydrofluoric acid, more preferably about 35 wt % hydrofluoric acid and 15 wt % hydrofluoric acid, and most preferably about 25 wt % hydrofluoric acid. When the first sample 20 comprises trichlorosilane it is preferred that the solution is about 25 wt % hydrofluoric acid.

As explained above, the first sample 20 preferably comprises less halosilane(s) than would react stoichiometrically with the aqueous hydrofluoric acid solution (e.g., based on the volume and composition of the solution). Halosilane(s) (e.g., chlorosilane(s)) added in greater than stoichiometric amounts to the aqueous hydrofluoric acid can result in the formation of undesired solids, unreacted halosilane(s), and/or loss of halosilane gas, all of which can affect the accurate determination of the amount of metal analytes present in the first sample 20.

In certain embodiments a halosilane (e.g., a chlorosilane) of the first sample 20 can react violently, if the first sample 20 is contacted with the aqueous hydrofluoric acid solution too rapidly. Reaction of certain halosilanes (e.g., trichlorosilane) with the aqueous hydrofluoric acid can generate heat. If the reaction is carried out rapidly, the liquid reaction mixture 30 can heat up quickly causing evaporation of components of the liquid reaction mixture 30, including impurities (i.e., metals), and reactants. Rapid increase in temperature of the reaction mixture can also make safe handling difficult. Furthermore, rapid introduction of the first sample 20 into the aqueous hydrofluoric acid can result in the accumulation of undesired solids (e.g., polysiloxanes and/or silica solids, among others). Such solids can build up at the interface between the first sample 20 and the aqueous hydrofluoric acid solution. If the first sample 20 is, for example, introduced into the aqueous hydrofluoric acid through the end of a subsurface tube, solids may accumulate and clog the end of the tube. While rapid contact between the first sample 20 and the aqueous hydrofluoric acid can be undesirable for these reasons, in practice it can be preferable that the reaction between the first sample 20 and the hydrofluoric acid solution occur in a relatively short time period. It is also preferred that the contact between the first sample 20 and the aqueous hydrofluoric acid solution is such that loss of any metals that were present in the first sample 20 is substantially reduced.

Preferably, the first sample 20 is contacted with a volume of aqueous hydrofluoric acid in such a way that the amount of halosilane from the first sample 20 that is reacted is substantially maximized; the loss of metals is substantially minimized; and the length of time required for the contact is substantially optimized. In one embodiment, the first sample 20 is contacted with the aqueous hydrofluoric solution at a flow rate of between about 0.5 g/min and 1 g/min, more preferably 1 g/min, when the volume of the aqueous hydrofluoric acid solution is between about 400 and 500 ml.

In order to help prevent the accumulation of undesired solids (e.g., polysiloxanes and/or silica solids, among others) at the contact interface between the first sample 20 and the aqueous hydrofluoric acid, a shield gas can be used, in certain embodiments. Even if the introduction of the first sample 20 into the aqueous hydrofluoric acid is performed relatively slowly, solids can accumulate at the site of contact between the halosilane of the first sample 20 and the hydrofluoric acid solution. A shield gas can be used to cause a first sample 20 to be diluted and shielded at the site that the first sample 20 contacts the acid solution. As a result of the physical relationship between the shield gas and the first sample 20, a liquid first sample 20 can become gaseous and/or form smaller droplets. A gaseous first sample 20 can be diluted by a shield gas as it comes into contact with the acid solution. The shield gas can, in certain embodiments, reduce accumulation of undesired solids at the contact interface. In one embodiment the shield gas does not chemically react with the first sample 20, the aqueous hydrofluoric acid, or the liquid reaction mixture 30. Preferably the shield gas is nitrogen, argon, or helium, more preferably nitrogen. Preferably, the shield gas is brought into contact with the first sample 20 such that accumulation of undesired solids is reduced at the contact interface between the first sample 20 and the aqueous hydrofluoric acid solution. Preferably the shield gas does not dissolve in the liquid reaction mixture 30 to a significant extent.

Preferably the liquid reaction mixture 30 that is produced by contacting the first sample 20 and the aqueous hydrofluoric acid solution comprises at least about 85% of at least one metal that was present in the first sample 20, more preferably at least about 90%, and most preferably at least about 95%. Liquid (e.g., including reaction products, such as fluorosilicic acid) is evaporated from the liquid reaction mixture 30 to near dryness thereby producing a near-dry residue 40. The liquid can be evaporated using methods known in the art. Preferably the liquid is evaporated under controlled temperature and pressure conditions. In one embodiment the liquid is evaporated under conditions, such that at least about 85% of any one metal present in the liquid reaction mixture 30 is present in the near-dry sample, more preferably at least about 90%, and most preferably at least about 95%. In one embodiment less than about 5 wt % of the liquid reaction mixture 30 is not evaporated, more preferably less than about 3 wt %, and most preferably less than about 1 wt %. Preferably the liquid reaction mixture 30 is evaporated until there is just a small droplet left.

The near-dry residue 40 is taken up in a take-up liquid to produce a second sample 50. At least a portion of the second sample 50 is analyzed for the presence of a detectable amount of at least one metal analyte. The take-up liquid used to take up the near-dry residue 40 is chosen to be compatible with the metal analyte detector that is to be used to analyze the second sample 50. The amount of take-up liquid used can depend on the type of detector (e.g., including detection limit) and the amount of metal present in the near-dry residue 40, among other factors. It is known in the art to determine the amount of the take-up liquid that can be used in preparing the second sample 50. If a dynamic reaction cell inductively coupled plasma-mass spectrometry (DRC ICP-MS) is used to analyze the second sample 50, the near-dry residue 40 can be taken up in a solution comprising nitric acid and hydrogen peroxide (e.g., 2% $HNO_3$ and 2% $H_2O_2$), preferably in a volume that is equal to the volume of the liquid reaction mixture 30 used for analysis. The amount of the second sample 50 that is analyzed depends on the detector that is used and the concentration of the second sample 50, among other factors, as is known in the art. The volume of the second sample 50 can be reduced to increase the concentrations of the metal analytes, thereby improving the detection limits.

Preferably, at least a portion of the second sample 50 is analyzed for the presence of at least one metal analyte that is selected from the group consisting of iron, molybdenum, chromium, zinc, magnesium, tin, titanium, nickel, copper, aluminum, boron, phosphorous, calcium, sodium, manganese, vanadium, potassium, lithium, beryllium, gallium, germanium, arsenic, strontium, zirconium, niobium, cobalt, silver, cadmium, indium, antimony, barium, tantalum, thallium, lead, and bismuth. More preferably, the at least one metal analyte that the second sample 50 is analyzed for is selected from the group consisting of boron, phosphorous, arsenic, antimony, germanium, iron, chromium, nickel, manganese, and molybdenum. Arsenic, antimony, germanium, arsenic, boron, and phosphorous can be used as dopants in semiconductors. Iron, chromium, nickel, manganese, and molybdenum can be components of stainless steel. (Stainless steel can be used in canisters or delivery systems in a fab, and a chlorosilane or tetrafluorosilane can become contaminated with corroded stainless steel from them.) Most preferably, the at least one metal analyte is selected from the group consisting of boron, phosphorus, and arsenic.

At least a portion of the second sample 50 can be analyzed for at least one metal analyte using any methods known in the art for that purpose. In one embodiment the analysis method can detect metals at concentrations less than about 1 ppbw (parts per billion by weight), more preferably at concentrations less than about 100 pptw (parts per trillion by weight), and most preferably at concentrations less than about 10 pptw. Preferably, the second sample is analyzed using graphite furnace atomic absorption (GFAA) or inductively coupled plasma-mass spectrometry (ICP-MS). More preferably, the second sample is performed using dynamic reaction cell inductively coupled plasma-mass spectrometry (DRC ICP-MS) or high resolution inductively coupled plasma-mass spectrometry.

Figure 2:
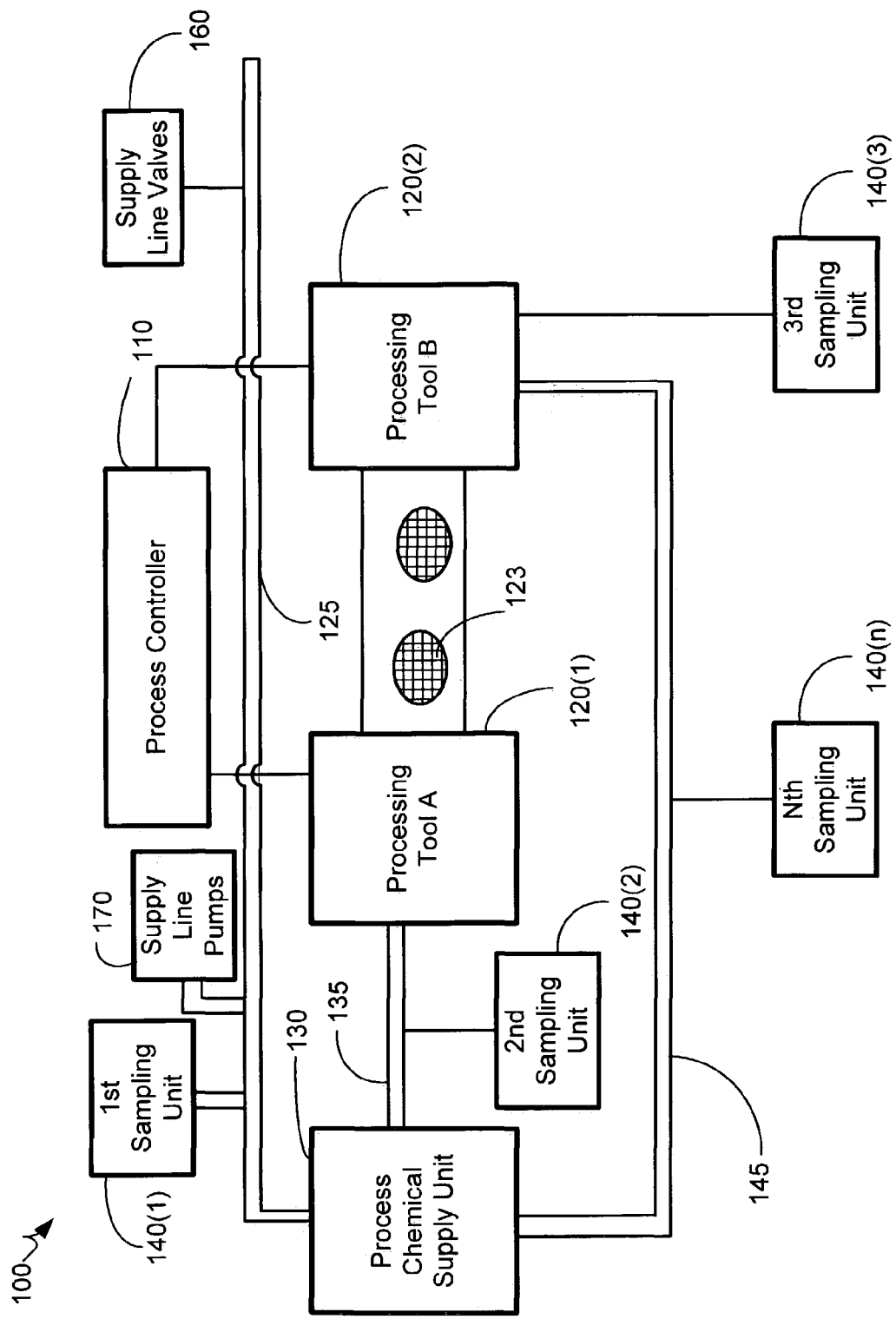
FIG. 2 depicts a system for sampling halosilanes in accordance with one embodiment of the present invention.

Turning now to FIG. 2, a block diagram illustration of a system 100 in accordance with embodiments of the present invention is illustrated. The system 100 may comprise a process controller 110 that is operatively coupled to a plurality of processing tools (e.g., processing tool A 120(1) and processing tool B 120(2)), collectively referred to with the reference number 120. The processing tools 120 may be capable of processing a workpiece 123, such as a semiconductor wafer. For example, processing tool A 120(1) and processing tool B 120(2) may be deposition tools. The processing tools 120 may receive chemical compounds including at least one halosilane (e.g., chlorosilane or fluorosilane) from a process chemical supply unit 130 for processing workpieces 123. The process chemical supply unit 130 comprising at least one halosilane may be capable of dispensing one or more compounds throughout the system 100.

The system 100 may comprise various sampling units 140(1-$n$) for acquiring chemical samples from various portions of the system 100. The process controller 110 is capable of controlling various aspects of the system 100, such as the processing tools 120, the sampling units 140(1-$n$), the process chemical supply unit 130, and, various supply line pumps 170 and valves 160. The process controller 110 may comprise a computer system that sends data to control the various units in the system 100. The process controller 110 may also receive and process data from the various components in the system 100.

The process chemical supply unit 130 may be directed to provide process chemical compounds (e.g., a chlorosilane or a fluorosilane) to the processing tools 120. The process chemical supply unit 130 is capable of dispensing compounds throughout the system 100 through various conduits or chemical supply lines. A supply line 125 provides chemical compounds comprising at least one halosilane to various apparatus within the system 100. The processing tool A 120(1) receives chemical compounds via a supply line 135. Processing tool B 120(2) receives process chemicals via a supply line 145. Various supply line valves 160 and/or supply line pumps 170 in the system 100 provide for flow-control of compounds throughout the system 100.

Various sampling units, i.e., the $1^{st}$-$N^{th}$ sampling units 140(1-$n$), which may be referred to collectively as sampling unit 140, may provide access to chemical samples from various portions of the system 100. For example the sampling units 140 may be tapped into the system 100 such that chemical samples comprising at least one halosilane being carried by the various supply lines 125, 135, 145 for purity analysis of the compounds may be extracted. Additionally, the sampling units 140 may be used to sample chemicals comprising at least one halosilane from portions of the processing tools 120. The first sampling unit 140(1) may be coupled to the supply line 125, a second sampling unit 140(2) may be coupled to the supply line 135, a third sampling unit 140(3) may be coupled to the processing tool B 120(2), and an N sampling unit 140($n$) may be coupled to the supply line 145.

As illustrated in FIG. 2, various sampling units 140(1-$n$) may be distributed throughout the system 100 at various points to sample the purity levels in the chemicals being transported and/or being used to process workpieces, such as semiconductor wafers. Therefore, an operator may assess the purity of the chemical compounds used in the processing of workpieces 123 at various time periods and at various points in the system 100. Although certain embodiments of the present invention are described in the context of a semiconductor processing system 100, implementation of embodiments of the present invention may be utilized in various types of process settings and remain within the spirit and scope of the present invention.

Figure 3:
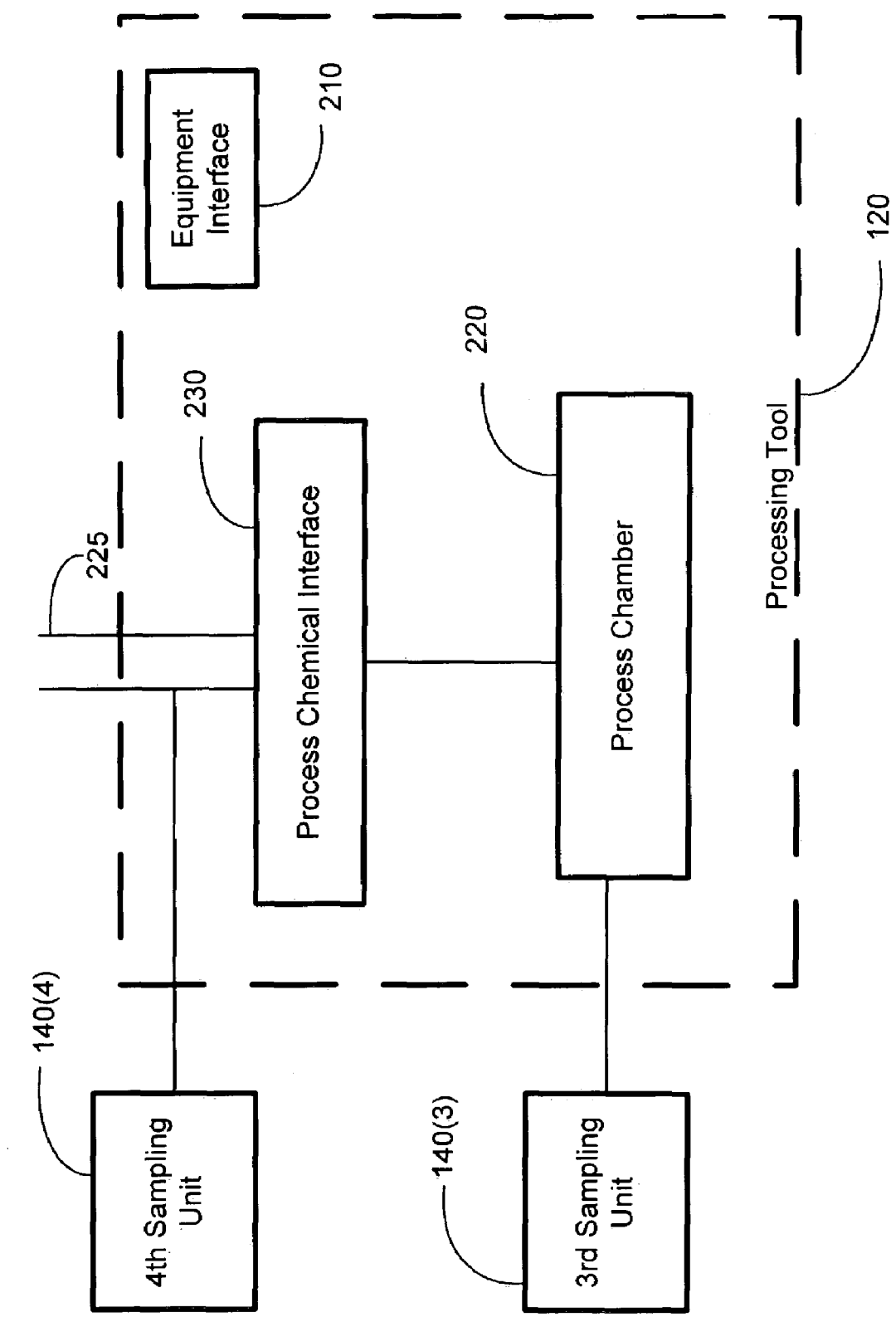
FIG. 3 depicts a processing tool associated with the system of FIG. 2.

Turning now to FIG. 3, a more detailed illustration of the processing tools 120 is illustrated. The processing tool 120 may comprise an equipment interface 210 that is capable of receiving and sending data to and from the process controller 110. The equipment interface 210 may receive data from the process controller 110 and provide responsive signals to various portions of the processing tool 120 for control of process operations. The equipment interface 210 may comprise data interfaces, processors, drivers, and the like, for receiving and sending data, as well as for generating control signals responsive to control data received from the process controller 110. Additionally, the equipment interface 210 may be capable of receiving various signals (e.g., status signals) from various components in the processing tool 120 and converting them into digital signals for transmission to the process controller 110.

The processing tool 120 comprises a process chamber 220. The process chamber 220 is capable of performing various processes, such as etch processes or deposition processes, and the like. The processing tool 120 also comprises a process chemical interface 230 that is coupled to a supply line 225. The process chemical interface 230 receives process chemical compounds and provides such chemical compounds to the process chamber 220. The process chemical interface 230 is capable of receiving the process chemicals and controlling the flow of such chemicals to the process chamber 220.

The third sampling unit 140(3) may be coupled to the process chamber 220 for sampling the chemicals being utilized by the process chamber 220 for processing semiconductor wafers. Additionally, a fourth sampling unit 140 (4) may be coupled to the incoming supply line 225 for sampling chemicals being received by the processing tool 120. The sampling units 140(3-4) provide the system 100 with the capability of directly analyzing the purity of chemical compounds being used by the processing tool 120 for processing workpieces 123 (e.g., semiconductor wafers). Therefore, throughout various points in the time period in which workpieces 123 are processed, the third and fourth sampling units 140(3-4) may be used to monitor the impurities in the chemicals being utilized by the processing tool 120.

Figure 4:
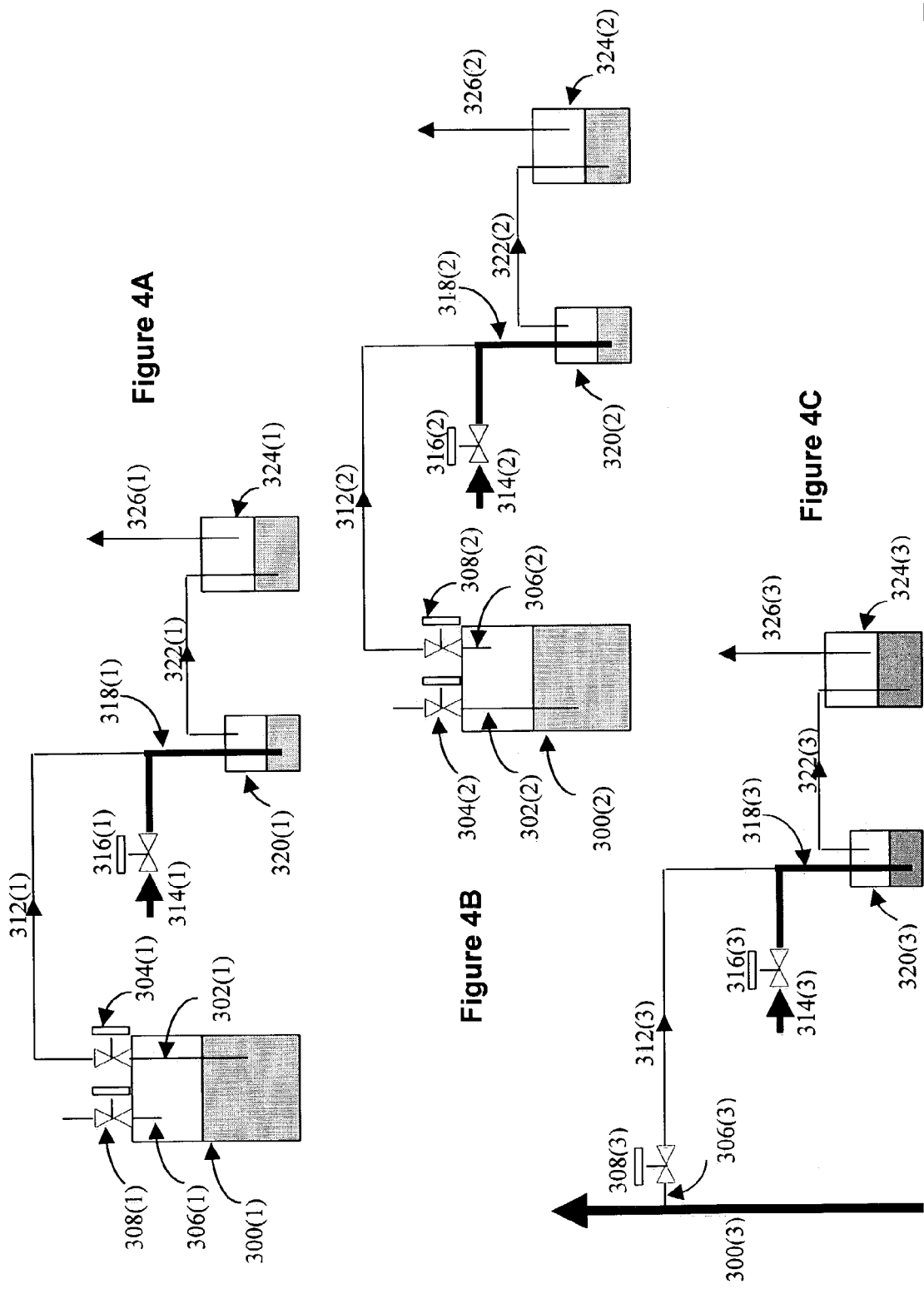
FIGS. 4A-4C depicts sampling systems in accordance with FIG. 2.

Turning now to FIG. 4, sampling of the present invention is depicted. In one embodiment, the depiction of FIGS. 4A-4C may be encompassed by the various sampling units 140. A halosilane source 300(1-3) is sampled. 300(1) and 300(2) depict halosilane sources, which may be canisters of liquefied halosilane (e.g., chlorosilane). The halosilane source 300(3) can be a halosilane supply line or a processing tool 120 (e.g., deposition chamber). In certain cases a liquid sample is removed and in other cases a gas sample is removed from the halosilane source 300. A halosilane canister comprises a gas port 306(1-2) and a liquid port 302(1-2). While FIG. 4C depicts a gas port 306(3), from the halosilane source 300(3) (e.g., supply line), a liquid port can be used to remove a liquid sample, when the halosilane source 300(3) comprises a liquid halosilane. Collection of a gas sample can be controlled by a gas port valve 308(1-3), while collection of a liquid sample can be controlled by a liquid port valve 304(1-2). For liquid sampling of a canister (FIG. 4A), the inert gas charge in the as-received canister (typically 20 psig) provides a sufficient driving force for collection of a liquid sample, when liquid port valve 304(1) is opened. If the inert gas charge is insufficient, the liquid port can be pressurized with an inert gas of sufficient pressure. For gas-phase sampling of a canister in FIG. 4B, the liquid port 302(2) can be pressurized with 15 psig nitrogen and halosilane-saturated nitrogen (e.g., 30% trichlorosilane by volume) can be withdrawn from the gas port valve 308(2).

A liquid or gas sample collected from a halosilane source 300 is carried by a sample introduction line 312(1-3) to an impinger 320(1-3). The sample introduction line 312 can comprise PTFE or PFA. The impinger 320 comprises a vessel containing an aqueous hydrofluoric acid solution. The sample introduction line 312 ends subsurface of the aqueous hydrofluoric acid. A shield gas can be drawn from a shield gas supply line 314(1-3), when a shield gas valve 316(1-3) is opened. The shield gas flows through a jacket 318(1-3) around the sample introduction line 312 and shields the sample as it is introduced into the aqueous hydrofluoric acid (see also FIG. 5). Halosilane (e.g., chlorosilane) of the sample introduced by the sample introduction line 312 reacts with aqueous hydrofluoric acid in the impinger 320 to produce a liquid reaction mixture 30. In certain embodiments, when the volume of the aqueous hydrofluoric acid at a concentration of between 49 wt % and 5 wt % is between about 400 and 500 ml, the halosilane (e.g., chlorosilane) sample can be introduced into the impinger 320 at a rate of about 1 g/min for about 45 minutes. A sample blank can be collected by passing nitrogen through the sampling system and bubbling through an identically prepared impinger 320 at the same rate for the same amount of time.

In certain cases, when the halosilane reacts with aqueous hydrofluoric acid in the impinger 320 to produce a liquid reaction mixture 30, an exhaust gas can be produced. The exhaust gas can be carried by an abatement line 322(1-3) to an abatement unit 324(1-3). The abatement unit 324 comprises an abatement vessel and an aqueous caustic solution (e.g., a sodium hydroxide solution or a calcium hydroxide solution). The exhaust gas can react with the caustic solution, and any gases released can be vented through vent 326(1-3). Vent gases can also go through further scrubbing.

Figure 5:
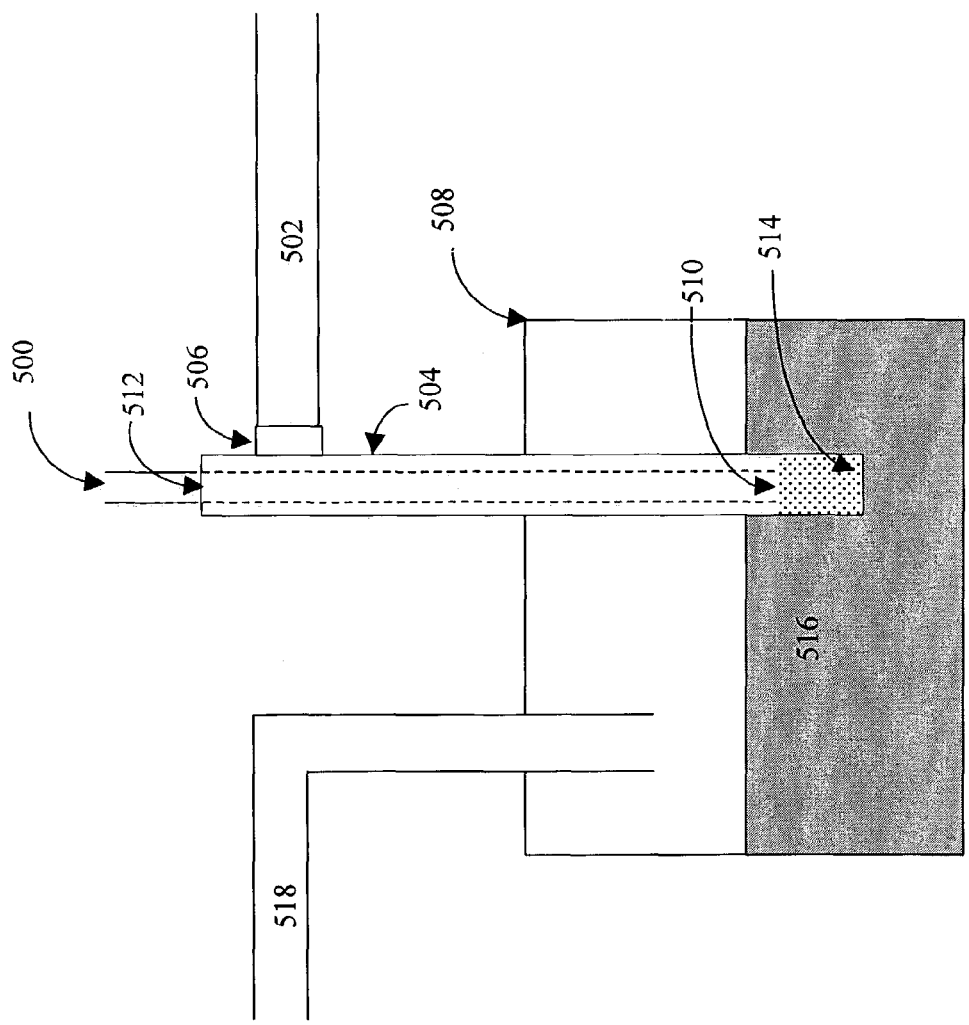
FIG. 5 depicts a shield gas introduction system and impinger in accordance with FIG. 4.

FIG. 5 is a depiction of a reaction system that comprises a sample introduction line 500 to carry the first sample 20, a shield gas supply line 502, a shield gas functional line 504, a connector 506, an impinger 508, and an abatement line 518. The shield gas supply line 502 and the shield gas functional line 504 are to carry a shield gas. The sample shield gas functional line 504 jackets at least a portion of the sample introduction line 500. The jacketed portion of the sample introduction line 500 comprises an open end 510 and a continuing end 512. The shield gas functional line 504 comprises an end that is sealed to the continuing end 512 of the portion of the sample introduction line 500 and an open end 514. A connector 506 connects the shield gas supply line 502 and the shield gas functional line 504, and the open end 510 of the jacketed portion of the sample introduction line 500 and the open end 514 of the shield gas functional line 504 are on the same side relative to the connector 506. The impinger 508 comprises a reaction vessel and the aqueous hydrofluoric acid solution 516. The open end 514 of the shield gas functional line 504 and the open end 510 of the jacketed portion of the sample introduction line 500 are positioned below the surface of the aqueous hydrofluoric acid solution 516. The open end 514 of the shield gas functional line 504 and the open end 510 of the sample introduction line 500 are positioned relative to one another such that when the shield gas and the first sample 20 are carried through the reaction system, the shield gas is capable of shielding the first sample 20 when the first sample 20 is contacted with the aqueous hydrofluoric acid solution to produce the liquid reaction mixture 30.

The open end 510 of the sample introduction line 500 is typically about one inch upstream of the open end 514 of the shield gas functional line 504. This arrangement largely prevents backstreaming and/or splashing of liquid and vapor into the open end of the sample introduction line 500, which would lead to closing of the open end 510 by silica solids. Positioning the open end 510 more than one inch upstream of the open end 514, may, in the case of liquid halosilane sampling, lead to undesired complete evaporation of the liquid halosilane and subsequent loss of metal analytes as dry deposits on the interior wall of the shield gas functional line 504, in certain embodiments.

In certain embodiments, any one of the sample introduction line 500, the shield gas supply line 502, the shield gas functional line 504, the connector 506, or the reaction vessel of the impinger 508 comprises polytetrafluoroethylene (PTFE) or perfluoroalkoxy (PFA). In certain embodiments, the connector 506 can be a tee connector. In certain embodiments, contacting the first sample 20 with the aqueous hydrofluoric acid solution in the impinger 508 further produces an exhaust gas. The exhaust gas can be removed by an abatement line 518 to an abatement unit 324(1-3).

The following example is included to demonstrate a representative embodiment of the invention. Those of skill in the art should, in light of the present disclosure, appreciate that many changes can be made in the specific embodiments which are disclosed and still obtain a like or similar result without departing from the spirit and scope of the invention.

EXAMPLE 1

A sampling system that comprised a TCS canister with vapor and liquid withdrawal ports, stainless steel hardware, PTFE and PFA hardware, a PTFE needle valve, and PFA tubing were used. The TCS canister, a sampling apparatus, and an abatement unit were contained in a gas cabinet. For liquid sampling, the inert gas charge in the as-received canister (typically 20 psig) provided a sufficient driving force. For gas-phase sampling, the liquid port was pressurized with 15 psig nitrogen and TCS-saturated nitrogen (estimated 30% TCS by volume) was withdrawn from the gas port.

TCS was handled in a manner similar to that used for dichlorosilane (DCS) in the industry. TCS has a higher boiling point (31.8° C. vs. 8.2° C.) than DCS. (See Table 1.) TCS is not pyrophoric in its pure form (autoignition temperature 182° C.), however the flammability limits are wide: LEL=1.2%, UEL=90.5%. The flashpoint for TCS is low, but higher than that of DCS (−14° C. vs. −52.2° C.). In addition, TCS is particularly susceptible to ignition in air by static discharge. TCS immediately hydrolyzes in the presence of moisture to form silica solids and hydrochloric acid (HCl), and thus is potentially very corrosive. Safe-handling of TCS required a ventilated work space, leak-free connections, and an inert gas purge of the sampling system both before and after TCS introduction.

Typically, TCS (gas or liquid phase) was sampled at 1 g/min. for 45 min. The TCS was brought into contact with 400-500 ml 25 wt % aqueous hydrofluoric acid solution in a sample bottle (e.g., impinger). The TCS was brought into contact with the HF(aq.) in the presence of a nitrogen shield gas. As explained in the discussion above, the sampling methods of the present invention can rely on the overall reaction of:

$$SiHCl_3 + 6HF(aq.) \rightarrow SiH_2F_6(aq.) + 3HCl(aq.) + H_2$$

This equation was used to calculate the quantity of TCS that was sampled in a test run, based on the weight gain of the impinger. The weight gain was not corrected for emissions of hydrogen, water vapor, HF, or HCl, which were all assumed to be small. The sample bottle (e.g., impinger) exhausted to an aqueous caustic scrubber. A sample blank was collected by passing nitrogen through the sampling system and bubbling through an identically prepared impinger for 45 min. The exothermicity of the reactions in the impinger were such that the temperature of the liquid in the impinger increased from room temperature to approximately 70° C., for a TCS sampling rate of 1 g/min (e.g., for about 45 minutes), added to 400 mL of 25 wt % aqueous HF in a 500 ml impinger bottle. Relevant physical data and references are found in Table 1.

TABLE 1

| Compound | Property | Value | Ref. |
|---|---|---|---|
| SiHCl$_3$ | Boiling pt. 1 atm. (° C.) | 31.8 | 2 |
| | Flash pt. (° C.) | −14 | 3 |
| | Autoignition temp. (° C.) | 182 | 1 |

TABLE 1-continued

| Compound | Property | Value | Ref. |
|---|---|---|---|
| | LEL/UEL (%) | 1.2/90.5 | 3 |
| SiH$_2$Cl$_2$ | Boiling pt. 1 atm. (° C.) | 8.2 | 2 |
| | Flash pt. (° C.) | −52.2 | 5 |
| | Autoignition temp. (° C.) | 44 | 1 |
| | LEL/UEL (%) | 4.1/98.8 | 4 |
| SiHCl$_3$ (g) | ΔH$_f$, 298° K., 1 atm. (kJ/mole) | −496.22 | 2 |
| SiH$_2$F$_6$ (aq.) | ΔH$_f$, 298° K., 1 atm. (kJ/mole) | −2379.4 | 6 |
| HF (aq.) | ΔH$_f$, 298° K., 1 atm. (kJ/mole) | −334.0 | 7 |
| HCl (aq.) | ΔH$_f$, 298° K., 1 atm. (kJ/mole) | −167.2 | 8 |
| H$_2$O (l) | ΔH$_f$, 298° K., 1 atm. (kJ/mole) | −285.8 | 8 |

The 400-500 mL hydrolysis solution from the impinger was slowly evaporated under carefully controlled temperature and pressure conditions to near-dryness. The near-dry residue was taken up in an aqueous solution of 2% HNO$_3$ [Fisher Optima grade] and 2% H$_2$O$_2$ [semiconductor grade] such that the volume was the same as the original sample volume. The sample prepared from the near-dry residue was analyzed by Dynamic Reaction Cell Inductively Coupled Plasma-Mass Spectrometry (DRC ICP-MS) (Perkin Elmer Elan 6000 DRC) for the presence of 34 metal analytes.

Metal concentrations detected in liquid-phase and gas-phase TCS are listed in Table 2. The concentrations of iron, molybdenum, and tin were higher in the liquid phase, whereas the concentrations of titanium and chromium were slightly higher in gas-phase TCS. The method detection limits were calculated as the greater of 0.1 ppbw or the sample blank concentration of the analyte. It should be noted that although the DRC ICP-MS detection limit was 1-10 pptw for most elements, the effect of sample dilution and environmental contaminants led to significantly higher method detection limits. The sampling portion of these laboratory-based tests was conducted in a non-clean room environment.

TABLE 2

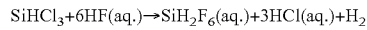

TCX Metal Analysis Results (unit = ppbw)

| Element | Det. Limit | Blank | Gas 1 | Gas 2 | Liquid 1 | Liquid 2 |
|---|---|---|---|---|---|---|
| Fe | 0.242 | 0.242 | <0.242 | <0.242 | 3.515 | 5.870 |
| Mo | <0.1 | <0.1 | <0.1 | <0.1 | 1.044 | 1.152 |
| Cr | 0.638 | 0.638 | 0.739 | 0.684 | <0.638 | <0.638 |
| Zn | 0.176 | 0.176 | <0.176 | 0.247 | <0.176 | <0.176 |
| Mg | 0.198 | 0.198 | <0.198 | 0.213 | 0.220 | 0.230 |
| Sn | <0.1 | <0.1 | <0.1 | <0.1 | 0.661 | 0.679 |
| Ti | 0.253 | 0.253 | 0.391 | 0.774 | <0.253 | <0.253 |
| Ni | <0.1 | <0.1 | <0.1 | <0.1 | <0.1 | 0.109 |
| Cu | <0.1 | <0.1 | <0.1 | <0.1 | <0.1 | 0.267 |
| Al | 0.154 | 0.154 | 0.185 | 0.168 | <0.154 | 0.340 |
| B | 0.165 | 0.165 | <0.165 | <0.165 | 0.302 | 0.327 |
| Ca | 0.187 | 0.187 | 0.326 | 0.213 | 0.452 | 0.376 |
| Na | 0.154 | 0.154 | <0.154 | 0.168 | <0.154 | <0.154 |
| Mn | <0.1 | <0.1 | <0.1 | <0.1 | <0.1 | <0.1 |
| V | <0.1 | <0.1 | <0.1 | <0.1 | <0.1 | <0.1 |
| K | <0.1 | <0.1 | <0.1 | <0.1 | <0.1 | <0.1 |
| Li | <0.1 | <0.1 | <0.1 | <0.1 | <0.1 | <0.1 |
| Be | <0.1 | <0.1 | <0.1 | <0.1 | <0.1 | <0.1 |
| Ga | <0.1 | <0.1 | <0.1 | <0.1 | <0.1 | <0.1 |
| Ge | <0.1 | <0.1 | <0.1 | <0.1 | <0.1 | <0.1 |
| As | <0.1 | <0.1 | <0.1 | <0.1 | <0.1 | <0.1 |
| Sr | <0.1 | <0.1 | <0.1 | <0.1 | <0.1 | <0.1 |
| Zr | <0.1 | <0.1 | <0.1 | <0.1 | <0.1 | <0.1 |
| Nb | <0.1 | <0.1 | <0.1 | <0.1 | <0.1 | <0.1 |
| Co | <0.1 | <0.1 | <0.1 | <0.1 | <0.1 | <0.1 |
| Ag | <0.1 | <0.1 | <0.1 | <0.1 | <0.1 | <0.1 |
| Cd | <0.1 | <0.1 | <0.1 | <0.1 | <0.1 | <0.1 |

TABLE 2-continued

TCX Metal Analysis Results (unit = ppbw)

| Element | Det. Limit | Blank | Gas 1 | Gas 2 | Liquid 1 | Liquid 2 |
|---------|------------|-------|-------|-------|----------|----------|
| In | <0.1 | <0.1 | <0.1 | <0.1 | <0.1 | <0.1 |
| Sb | <0.1 | <0.1 | <0.1 | <0.1 | <0.1 | <0.1 |
| Ba | <0.1 | <0.1 | <0.1 | <0.1 | <0.1 | <0.1 |
| Ta | <0.1 | <0.1 | <0.1 | <0.1 | <0.1 | <0.1 |
| Tl | <0.1 | <0.1 | <0.1 | <0.1 | <0.1 | <0.1 |
| Pb | <0.1 | <0.1 | <0.1 | <0.1 | <0.1 | <0.1 |
| Bi | <0.1 | <0.1 | <0.1 | <0.1 | <0.1 | <0.1 |

A spike recovery test was performed for the 34 elements listed in Table 3. Four sample bottles were prepared, each containing 400 g 25 wt % aqueous HF. Two of the bottles were spiked with 80 ng of each element in Table 3; the other two bottles were unspiked controls. Each of the four bottles was then used to sample approximately 45 g liquid-phase TCS following the procedure described above. Table 3 displays recovery percentages calculated based on the following relationship:

$$SR_A(\%) = 100\% * ([A]\text{spike} - [A]\text{unspiked})/200 \text{ pptw}$$

where, $SR_A(\%)$ = percent spike recovery of element A
[A]spike = avg. concentration of A in spiked samples
[a]unspiked = avg. concentration of A in unspiked samples
200 pptw = parts-per-trillion-weight spike concentration

TABLE 3

Spike Recovery Results

| Element | Spike Recovery % | Element | Spike Recovery (%) |
|---------|------------------|---------|---------------------|
| Li | 92 | Ga | 94 |
| Be | 94 | Ge | 88 |
| B | 94 | As | 95 |
| Na | 91 | Sr | 90 |
| Mg | 93 | Zr | 90 |
| Al | 91 | Nb | 96 |
| K | 92 | Mo | 83 |
| Da | 85 | Ag | 85 |
| Ti | 93 | Cd | 93 |
| V | 92 | In | 90 |
| Cr | 89 | Sn | 89 |
| Mn | 93 | Sb | 89 |
| Fe | 112 | Ba | 89 |
| Co | 97 | Ta | 88 |
| Ni | 115 | Tl | 89 |
| Cu | 97 | Pb | 91 |
| Zn | 97 | Bi | 88 |

The sampling and evaporation techniques of the present invention yielded recoveries of between 83% and 115% for all elements. Excellent recoveries were obtained for dopant elements (B, As, Sb, and Fe) as well as for stainless steel components (Fe, Cr, Ni, Mn, and Mo) that are typically found in TCS specifications.

Supplier reported specifications for metals in TCS are usually restricted to Fe, B, P, and/or 'total donors'. The levels of these metals in supplier TCS are expressed as ppba (parts-per-billion-atom) in an epitaxial silicon layer (e.g., film) deposited from the gas, and the layer is analyzed by photoluminescence spectroscopy. Table 4 compares industry standard TCS metal impurity specifications with method detection limits of the present invention. (Note that for this comparison no attempt was made to estimate the degree to which each metal impurity in TCS would be incorporated into the silicon film).

TABLE 4

Detection Limits vs. TCS Metal Specifications

| Element | Specification (ppba) | Sample Blank (ppbw) |
|---------|----------------------|----------------------|
| Fe | 5 | 0.2-1.2 |
| B | 0.1-0.3 | 0.1-0.2 |
| P | 1 | — |
| Total Donor | 0.8-1.5 | — |

From these data, and from the data in Table 3, it can be concluded that the detection limits of sampling methods of the present invention are sufficient to verify that a TCS sample is within the specification range for iron, (and therefore free from corrosion-related contamination) as well as for the dopants As, Sb, and Ge.

All of the methods disclosed and claimed herein can be made and executed without undue experimentation in light of the present disclosure. It will be apparent to those of skill in the art that variations may be applied to the methods and in the steps or in the sequence of steps of the method described herein without departing from the concept, spirit and scope of the invention. All substitutes and modifications apparent to those skilled in the art are deemed to be within the spirit, scope and concept of the invention as defined by the appended claims.

REFERENCES

1. L. G. Britton and P. Taylor, *Semicond. Intl.*, 182, (May, 1991).
2. NIST Webbook, http://webbook.nist.gov/chemistry/
3. Air Liquide Material Safety Data Sheet-Trichlorosilane
4. Air Liquide Material Safety Data Sheet-Dichlorosilane
5. Praxair Material Safety Data Sheet-Dichlorosilane
6. *J. Phys. Chem. Ref Data*, 11(2), 2-112 (1982).
7. JANAF Thermochemical Tables, *Nat. Stand. Ref Data Ser.*, 37, (1971).
8. K. J. Laidler and J. H. Meiser, *Physical Chemistry*, p. 66 (1982).

What is claimed is:

1. A system for measuring at least one metal analyte from a halosilane source, comprising:

(a) a halosilane source comprising at least one halosilane having a formula $Si_u Cl_v F_w Br_x I_y N_z$, wherein u is 1 or 2; (v+w+x+y) is an integer between 1 and 4+2(u−1), inclusive; each of v, w, x, and y is an integer between 0 and 4+2(u−1), inclusive; z is an integer between 0 and 2u+1, inclusive; (v+w+x+y+z) is equal to 4+2(u−1); and each N is independently selected from the group consisting of hydrogen, methyl, methoxy, ethyl, ethoxy, propyl, propoxy, isopropyl, isopropoxy, n-butyl, butoxy, vinyl, and phenyl, (b) at least one reaction system coupled to said halosilane source, wherein a first sample comprising the halosilane is collected from the halosilane source, wherein the first sample and an aqueous hydrofluoric acid solution are contacted in the reaction system to produce a liquid reaction mixture, and the reaction system comprises:

a sample introduction line to carry the first sample,
a shield gas supply line,
a shield gas functional line,
   wherein the shield gas supply line and the shield gas functional line are to carry a shield gas, wherein the shield gas functional line has a longitudinal axis that is parallel to the longitudinal axis of the sample introduction line, and the sample shield gas functional line jackets at least a portion of the sample introduction line, wherein the jacketed portion of the sample introduction line comprises an open end and a continuing end, and wherein the shield gas functional line comprises a first end that is sealed to the continuing end of the portion of the sample introduction line and an open end, a connector that connects the shield gas supply line and the shield gas functional line, wherein the open end of the jacketed portion of the sample introduction line and the open end of the shield gas functional line are on the same side relative to the connector, and an impinger comprising a reaction vessel and the aqueous hydrofluoric acid solution therein, wherein the open end of the shield gas functional line and the open end of the jacketed portion of the sample introduction line are positioned below the surface of the aqueous hydrofluoric acid solution, and wherein the open end of the shield gas functional line and the open end of the sample introduction line are positioned relative to one another such that when the shield gas and the first sample are carried through the reaction system, the shield gas is capable of shielding the first sample when the first sample is contacted with the aqueous hydrofluoric acid solution, thereby producing the liquid reaction mixture, (c) an evaporator, wherein the evaporator is used to evaporate liquid from the liquid reaction mixture to produce a near-dry residue, wherein the near-dry residue is mixed with a take-up liquid to produce a second sample, and (d) a metal analyte detector, wherein the metal analyte detector is used to analyze the second sample for the presence of a detectable amount of at least one metal analyte.

2. The system of claim 1, wherein the halosilane source is selected from the group consisting of a halosilane canister, a halosilane bulk storage tank, halosilane supply line, and a deposition chamber.

3. The system of claim 1, wherein the halosilane source is a chlorosilane source comprising at least one chlorosilane.

4. The system of claim 1, wherein at least one of the sample introduction line, the shield gas supply line, the shield gas functional line, the connector, or the reaction vessel comprises polytetrafluoroethylene (PTFE).

5. The system of claim 1, wherein at least one of the sample introduction line, the shield gas supply line, the shield gas functional line, the connector, or the reaction vessel comprises perfluoroalkoxy (PFA).

6. The system of claim 1, wherein the connector is a tee connector.

7. The system of claim 1, wherein the aqueous hydrofluoric acid solution comprises between about 49 wt % and 5 wt % hydrofluoric acid.

8. The system of claim 1, wherein contacting the first sample with the aqueous hydrofluoric acid solution in the impinger further produces an exhaust gas, and wherein the reaction system further comprises an abatement line and an abatement unit, wherein the abatement line is capable of carrying the exhaust gas from the impinger to the abatement unit, and the abatement unit comprises an abatement vessel and an aqueous caustic solution.

9. The system of claim 1, wherein the detector uses graphite furnace atomic absorption (GFAA) or inductively coupled plasma-mass spectrometry (ICP-MS).

10. The system of claim 1, wherein the detector is capable of detecting at least one metal analyte selected from the group consisting of boron, phosphorous, arsenic, antimony, germanium, iron, chromium, nickel, manganese, and molybdenum.

11. The system of claim 1, wherein the detector is capable of detecting less than about one ppbw of at least one metal analyte.

12. The system of claim 1, wherein each of w, x, and y is 0.

13. A system for sampling for at least one metal analyte in a halosilane supply, comprising:

(a) a halosilane supply line to transport at least one halosilane having a formula $Si_uCl_vF_wBr_xI_yN_z$, wherein u is 1 or 2; (v+w+x+y) is between 1 and 4+2(u−1), inclusive; each of v, w, x, and y is between 0 and 4+2(u−1), inclusive; z is between 0 and 2u+1; (v+w+x+y+z) is equal to 4+2(u−1); and each N is independently selected from the group consisting of hydrogen, methyl, methoxy, ethyl, ethoxy, propyl, propoxy, isopropyl, isopropoxy, n-butyl, butoxy, vinyl, and phenyl, (b) a sampling unit coupled with said halosilane supply line, wherein (i) said sampling unit collects a first sample from the halosilane supply line, wherein the first sample comprises the halosilane; and contacts the first sample with an aqueous hydrofluoric acid solution, thereby producing a liquid reaction mixture, wherein at least one chemical reaction occurs as a result of the contacting step, wherein the chemical reaction comprises the halosilane reacting with the aqueous hydrofluoric acid, and (ii) said sampling unit, comprises:

a sample introduction line to carry the first sample;

a shield gas supply line;

a shield gas functional line, wherein the shield gas supply line and the shield gas functional line are to carry a shield gas, wherein the shield gas functional line has a longitudinal axis that is parallel to the longitudinal axis of the sample introduction line, and the sample shield gas functional line jackets at least a portion of the sample introduction line, wherein the jacketed portion of the sample introduction line comprises an open end and a continuing end, and wherein the shield gas functional line comprises a first end that is sealed to the continuing end of the portion of the sample introduction line and an open end;

a connector that connects the shield gas supply line and the shield gas functional line, wherein the open end of the jacketed portion of the sample introduction line and the open end of the shield gas functional line are on the same side relative to the connector;

an impinger comprising a reaction vessel and the aqueous hydrofluoric acid solution therein, wherein the open end of the shield gas functional line and the open end of the jacketed portion of the sample introduction line are positioned below the surface of the aqueous hydrofluoric acid solution, and wherein the open end of the shield gas functional line and the open end of the sample introduction line are positioned relative to one another such that when the shield gas and the first sample are carried through the sampling unit, the shield gas is capable of shielding the first sample when the first sample is contacted with the aqueous hydrofluoric acid solution, thereby producing the liquid reaction mixture and at least one exhaust gas;

an abatement line; and an abatement unit comprising an abatement vessel and an aqueous caustic solution, wherein the abatement line is capable of carrying the exhaust gas from the impinger to the abatement unit.

14. The system of claim 13, wherein each w, x, and y is 0.

15. A system, comprising:
(a) a processing tool to process workpieces,
(b) a halosilane supply line coupled to said processing tool, said halosilane supply line to supply at least one of trichlorosilane, dichlorosilane, tetrachlorosilane, and tetrafluorosilane for said processing of workpieces,
(c) a sampling unit coupled to the tool and halosilane supply line, wherein
(i) said sampling unit collects a first sample from the halosilane supply line,
wherein the first sample comprises at least one of trichlorosilane, dichlorosilane, tetrachlorosilane, and tetrafluorosilane; and contacts the first sample with an aqueous hydrofluoric acid solution, thereby producing a liquid reaction mixture,
wherein at least one chemical reaction occurs as a result of the contacting step, wherein the chemical reaction comprises the halosilane reacting with the aqueous hydrofluoric acid, and
(ii) said sampling unit, comprises:
a sample introduction line to carry the first sample;
a shield gas supply line;
a shield gas functional line,
wherein the shield gas supply line and the shield gas functional line are to carry a shield gas, wherein the shield gas functional line has a longitudinal axis that is parallel to the longitudinal axis of the sample introduction line, and the sample shield gas functional line jackets at least a portion of the sample introduction line, wherein the jacketed portion of the sample introduction line comprises an open end and a continuing end, and wherein the shield gas functional line comprises a first end that is sealed to the continuing end of the portion of the sample introduction line and an open end;

a connector that connects the shield gas supply line and the shield gas functional line;

wherein the open end of the jacketed portion of the sample introduction line and the open end of the shield gas functional line are on the same side relative to the connector; and an impinger comprising a reaction vessel and the aqueous hydrofluoric acid solution therein, wherein the open end of the shield gas functional line and the open end of the jacketed portion of the sample introduction line are positioned below the surface of the aqueous hydrofluoric acid solution, and wherein the open end of the shield gas functional line and the open end of the sample introduction line are positioned relative to one another such that when the shield gas and the first sample are carried through the sampling unit, the shield gas is capable of shielding the first sample when the first sample is contacted with the aqueous hydrofluoric acid solution, thereby producing the liquid reaction mixture.

16. The system of claim 15, wherein the first sample comprises trichlorosilane.

17. The system of claim 15, further comprising a process controller coupled to the processing tool, the halosilane supply line, and the sampling unit, said process controller to control an operation of at least one of the processing tool, the halosilane supply line, and the sampling unit.

18. The system of claim 15, wherein the workpieces are semiconductor wafers.

* * * * *